US011602617B2

(12) United States Patent
Bonnette

(10) Patent No.: US 11,602,617 B2
(45) Date of Patent: Mar. 14, 2023

(54) PUMPLESS THROMBECTOMY SYSTEM

(71) Applicant: Michael Bonnette, Minneapolis, MN (US)

(72) Inventor: Michael Bonnette, Minneapolis, MN (US)

( * ) Notice: Subject to any disclaimer, the term of this patent is extended or adjusted under 35 U.S.C. 154(b) by 0 days.

(21) Appl. No.: 16/853,615

(22) Filed: Apr. 20, 2020

(65) Prior Publication Data

US 2021/0060311 A1 Mar. 4, 2021

Related U.S. Application Data

(60) Provisional application No. 62/835,919, filed on Apr. 18, 2019.

(51) Int. Cl.
*A61M 25/10* (2013.01)
*A61J 1/14* (2006.01)

(52) U.S. Cl.
CPC ............ *A61M 25/10* (2013.01); *A61J 1/1406* (2013.01); *A61M 2025/109* (2013.01); *A61M 2025/1052* (2013.01)

(58) Field of Classification Search
CPC ............ A61J 1/1406; A61B 2217/005; A61B 2217/007; A61B 17/3207; A61B 2017/22079; A61B 2017/22082; A61B 2017/22084; A61M 25/007; A61M 2005/14513; A61M 5/142224; A61M 5/14593; A61M 5/14513
See application file for complete search history.

(56) References Cited

U.S. PATENT DOCUMENTS

| 1,869,443 | A | * | 8/1932 | Stocklin ............ A61M 5/14526 604/246 |
| 5,674,433 | A | | 10/1997 | Semmens et al. |
| 5,989,271 | A | | 11/1999 | Bonnette et al. |
| 6,224,570 | B1 | | 5/2001 | Le et al. |
| 6,676,637 | B1 | | 1/2004 | Bonnette et al. |
| 6,764,483 | B1 | | 7/2004 | Bonnette et al. |
| 6,932,828 | B2 | | 8/2005 | Bonnette et al. |

(Continued)

FOREIGN PATENT DOCUMENTS

| EP | 1092396 A8 | 4/2001 |
| EP | 1865858 B1 | 11/2005 |

(Continued)

*Primary Examiner* — Theodore J Stigell
*Assistant Examiner* — Rachel T. Smith
(74) *Attorney, Agent, or Firm* — Lance M. Pritikin

(57) ABSTRACT

A thrombectomy catheter system can include a catheter configured for insertion into vasculature of a patient. The system includes a pressure chamber configured to isolate an internal volume from a surrounding environment. The system can include an infusion container including an infusion fluid therein. The pressure chamber can receive the infusion container. A drive unit can pressurize a working fluid in the pressure chamber with the infusion container received in the pressure chamber. In an example, pressurizing of the working fluid correspondingly compresses the infusion container to pressurize the infusion fluid and transfer the infusion fluid to the catheter. In an example, the infusion fluid is isolated from the working fluid by the infusion container when the working fluid is pressurized in the pressure chamber.

16 Claims, 9 Drawing Sheets

(56) References Cited

U.S. PATENT DOCUMENTS

| | | |
|---|---|---|
| 6,942,678 B2 | 9/2005 | Bonnette et al. |
| 7,169,161 B2 | 1/2007 | Bonnette et al. |
| 7,219,799 B2 | 5/2007 | Bonnette et al. |
| 7,220,243 B2 | 5/2007 | Bonnette et al. |
| 7,334,681 B2 | 2/2008 | Bonnette et al. |
| 7,615,031 B2 | 11/2009 | Bonnette et al. |
| 7,846,175 B2 | 12/2010 | Bonnette et al. |
| 7,996,974 B2 | 8/2011 | Kozak et al. |
| 3,012,117 A1 | 9/2011 | Bonnette et al. |
| 8,157,766 B2 | 4/2012 | Bonnette et al. |
| 8,439,878 B2 | 5/2013 | Bonnette et al. |
| 8,475,487 B2 | 7/2013 | Bonnette et al. |
| 8,657,777 B2 | 2/2014 | Kozak et al. |
| 8,974,418 B2 | 3/2015 | Bonnette et al. |
| 8,998,843 B2 | 4/2015 | Bonnette et al. |
| 9,005,163 B2 | 4/2015 | Bonnette et al. |
| 9,108,019 B2 | 8/2015 | Bonnette et al. |
| 9,149,609 B2 | 10/2015 | Ansel et al. |
| 9,238,119 B2 | 1/2016 | Thor et al. |
| 9,585,686 B2 | 3/2017 | Riles et al. |
| 9,855,070 B2 | 1/2018 | Bonnette et al. |
| 9,901,361 B2 | 2/2018 | Morris et al. |
| 10,076,404 B2 | 9/2018 | Bonnette |
| 10,321,932 B2 | 6/2019 | Bonnette et al. |
| 10,828,061 B2 | 11/2020 | Bonnette et al. |
| 10,850,066 B2 | 12/2020 | Uber, III et al. |
| 10,869,990 B2 | 12/2020 | Bonnette et al. |
| 2005/0182437 A1 | 8/2005 | Bonnette et al. |
| 2006/0064071 A1 | 3/2006 | Bonnette et al. |
| 2007/0201993 A1* | 8/2007 | Terentiev .............. F04B 43/113 417/393 |
| 2008/0234722 A1 | 9/2008 | Bonnette et al. |
| 2008/0275383 A1 | 11/2008 | Weisel et al. |
| 2008/0275393 A1 | 11/2008 | Bonnette et al. |
| 2008/0275397 A1 | 11/2008 | Bonnette |
| 2008/0287986 A1 | 11/2008 | Thor et al. |
| 2008/0319386 A1 | 12/2008 | Bonnette et al. |
| 2009/0156983 A1 | 6/2009 | Bonnette et al. |
| 2014/0214060 A1 | 7/2014 | Bonnette et al. |
| 2014/0228869 A1 | 8/2014 | Bonnette et al. |
| 2014/0277006 A1 | 9/2014 | Bonnette et al. |
| 2014/0303658 A1* | 10/2014 | Bonnette ........... A61B 17/32075 606/159 |
| 2015/0051487 A1 | 2/2015 | Uber, III et al. |
| 2015/0151101 A1 | 6/2015 | Bonnette et al. |
| 2017/0340343 A1 | 11/2017 | Bonnette et al. |
| 2018/0296752 A1 | 10/2018 | Bonnette et al. |
| 2018/0369457 A1* | 12/2018 | Borgmeier .............. A61M 1/80 |
| 2019/0290315 A1 | 9/2019 | Bonnette et al. |

FOREIGN PATENT DOCUMENTS

| | | | |
|---|---|---|---|
| EP | 2211972 B1 | 12/2015 | |
| EP | 1696966 B1 | 4/2017 | |
| EP | 2866701 B1 | 12/2019 | |
| EP | 3756721 A1 | 12/2020 | |
| JP | 2006014749 * | 1/2006 | |
| WO | 199607471 A1 | 3/1996 | |
| WO | 2003000311 A3 | 1/2003 | |
| WO | 2003000316 A1 | 1/2003 | |
| WO | 2003039624 A2 | 5/2003 | |
| WO | WO-2008130715 A2 * | 10/2008 | ........... A61F 7/0085 |
| WO | 2008157077 A1 | 12/2008 | |
| WO | 2009094041 A1 | 7/2009 | |
| WO | 2014065969 A1 | 5/2014 | |
| WO | 2014158816 A1 | 10/2014 | |
| WO | 2014159204 A3 | 10/2014 | |
| WO | 2015196156 A1 | 12/2015 | |
| WO | 2016033351 A3 | 3/2016 | |
| WO | 2018013825 A2 | 1/2018 | |

* cited by examiner

PUMPLESS THROMBECTOMY SYSTEM

CLAIM OF PRIORITY

This patent application claims the benefit of priority of Bonnette, U.S. Provisional Patent Application Ser. No. 62/835,919, entitled "PUMPLESS THROMBECTOMY SYSTEM." filed on Apr. 18, 2019, which is hereby incorporated by reference herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Michael Bonnette, Minneapolis, Minn. All Rights Reserved.

TECHNICAL FIELD

This document pertains generally, but not by way of limitation, to catheter systems using an operating fluid.

BACKGROUND

In an example, a catheter is utilized to macerate (e.g., dislodge, dismember, cut, chop, break up, remove, or the like) a thrombus within a patient. For example, the catheter mechanically engages with the thrombus to macerate the thrombus. The catheter includes suction to facilitate removal of the thrombus (or macerated thrombus) from the patient (e.g., by evacuating thrombus from vasculature of a patient). For example, a vacuum source is in communication with a suction lumen of the catheter, and operation of the vacuum source draws thrombus into the suction lumen.

Overview

The high pressure, thrombectomy field includes designs with various levels of effectiveness. The designs are compatible with basic procedures encountered in the interventional medical field. For example, a catheter is threaded through a vein or artery which performs a function within the body at a tip of the catheter or along a length of the catheter. In an example, the catheter is attached to a drive unit (e.g., an electromechanical drive unit, or the like). For example, the drive unit includes one or more of a metal pump, plastic pump, contrast injection equipment having syringes, or the like. In some examples, components of the drive unit and the catheter include disposable hardware.

The present subject matter includes a catheter system. In an example, the catheter system includes one or more mechanical disrupters, for example a mechanical disruptor that engages with thrombus to macerate the thrombus. For example, the disruptors utilize one or more of mechanical engagement with the thrombus or pressurizing fluids to engage with thrombus. Accordingly, the disruptors facilitate maceration of the thrombus. Maceration of the thrombus enhances removal of the thrombus, for instance because the thrombus is dissected into smaller pieces which eases removal of the thrombus from vasculature of a patient.

The catheter system optionally includes a vacuum source (e.g., suction source, or the like), for instance a mechanical vacuum source or a fluid vacuum sources (e.g., fluid power utilizing a venturi effect, Bernoulli principle, or the like). In some examples, the catheter system includes a pump that is disposable for sanitary purposes or is rated for a single use. The pump develops pressure, suction, or the like to facilitate macerating or evacuating thrombus from a human body. The disposable (e.g., non-reusable, single-use, or the like) component adds cost to the device and additional procedures for operating the catheter system. For instance, the pump is not reusable due to the complexity of sterilization of the catheter system, or other cost justifications. In another example, the disposable component adds complexity to the design of the catheter system.

Examples of catheter assemblies are described herein that are 'pumpless' (e.g., include a fluid moving mechanism that is isolated from biological or biological interacting fluids). For example, the example catheter systems include a pump that is reusable. In an example, the pump does not need to be disposed of. Accordingly, the pumpless catheter system reduces cost and complexity of the catheter assemble (e.g., a thrombectomy catheter, or the like). This disclosure describes the pumpless drive unit design, and a variety of new thrombectomy catheter designs. For example, the system and components described herein enhance the efficient and minimize costs for performing thrombectomy (e.g., in an interventional setting).

In an example, the pumpless catheter system includes a pressure chamber. An infusion fluid is contained in an infusion container, and the infusion container is optionally located in the pressure chamber. The infusion container is in fluidic communication with a catheter, and accordingly infusion fluid is allowed flow to the catheter from the infusion container. For example, the infusion container is compressed in the pressure chamber to transfer infusion fluid from the infusion container to the catheter.

In one example, a working fluid is pumped into the pressure chamber, and the working fluid is in communication with and pressurizes the infusion container. The working fluid is optionally a non-compressible (or low-compressible) fluid (e.g., a liquid, or the like). Optionally, the infusion container is deformable, for instance with the infusion container including a bag, or the like. Optionally, the working fluid is pressurized, for instance with a pump, such as an isolated pump separated from the infusion fluid. In an example, the working fluid is pumped into the pressure chamber with the infusion container located in the pressure chamber. The working fluid in the pressure chamber is pressurized (e.g., with the pump), and accordingly the pressure of the working fluid is applied to the infusion container and the infusion fluid therein. For instance, the pressure of the working fluid applied to the infusion container causes the infusion fluid to flow from the infusion container toward the catheter.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
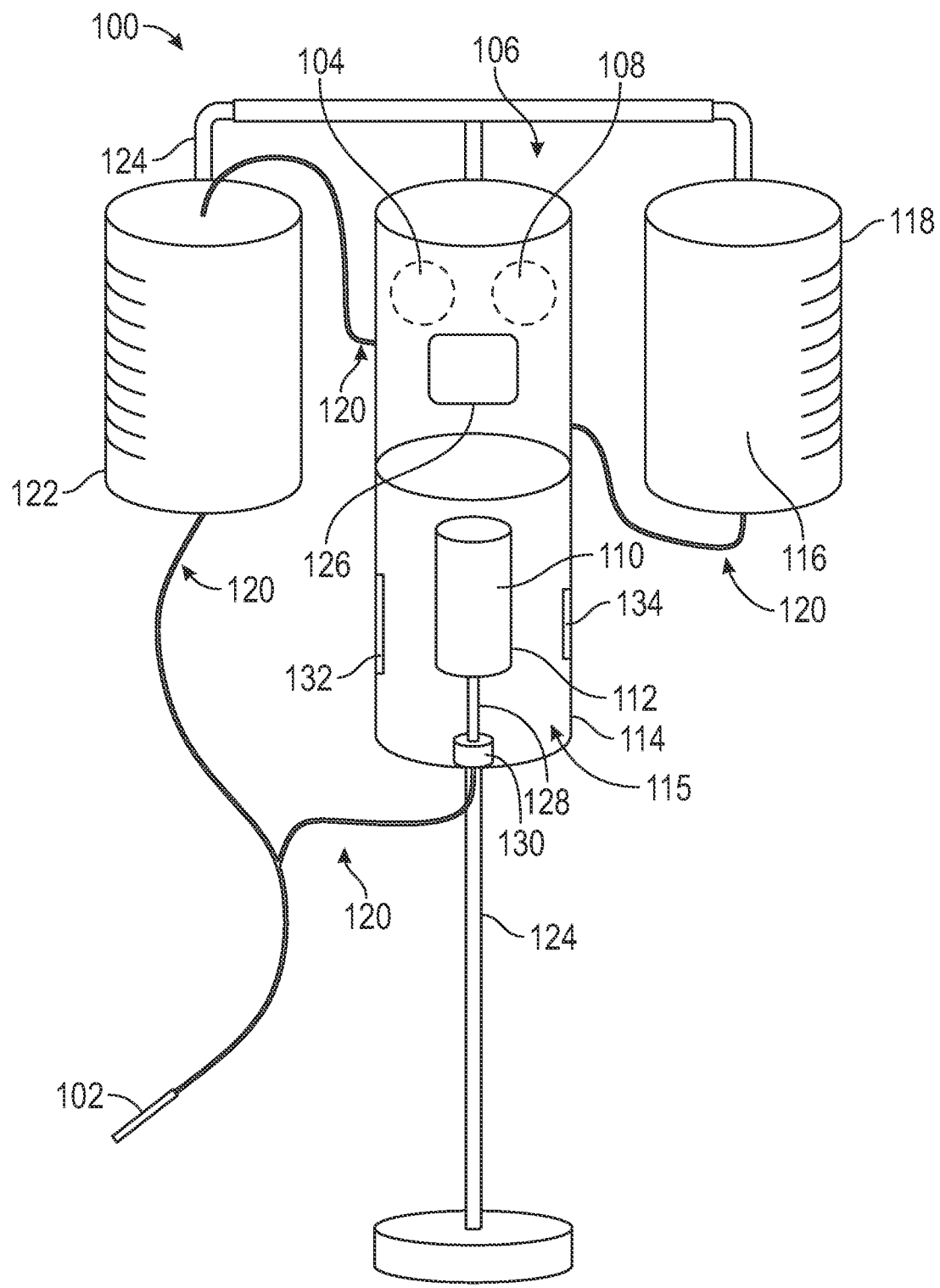
FIG. 1 illustrates a front view of an example of a catheter system.

FIG. 1 illustrates a front view of an example of a catheter system 100, for instance a thrombectomy catheter assembly. The catheter system 100 includes a catheter 102. In some examples, the catheter 102 is located in vasculature of a patient, for instance by inserting the catheter 102 into a vein (e.g., through a penetration along the leg, arm or the like). The catheter 102 facilitates removal of a thrombus from the vasculature of a patient. For example, the catheter 102 is utilized to macerate a thrombus (including one or more of parting, division, breaking up, compression or the like) in vasculature of a patient. The catheter system 100 includes a vacuum source 104 configured to provide a relative negative (e.g., lower) pressure, and the vacuum source 104 facilitates removal of thrombus. For instance, the vacuum source 104 is in communication with the catheter 102, and the vacuum source 104 generates a vacuum. The vacuum draws the thrombus into the catheter 102, for instance to remove the thrombus from vasculature of the patient.

The catheter system 100 includes a drive unit 106, and the drive unit 106 facilitates removal of thrombus in vasculature of a patient. For example, the drive unit 106 includes the vacuum source 104. The drive unit 106 optionally includes a pump 108 that is isolated from infusion fluids described herein and isolated from fluids or features of the system that interact with biological tissues, fluids or the like (e.g., the catheter system is pumpless in that the pump is isolated from the remainder of the system while still moving one or more fluids, such as the infusion fluid). In an example, the pump 108 (or the vacuum source 104) includes a positive displacement pump (e.g., rotary, reciprocating, linear, or the like) including reciprocating pistons or the like. In another example the pump 108 is a peristaltic pump, a syringe, or the like.

The pump 108 facilitates removal of a thrombus. In an example, the pump 108 facilitates pressurizing an infusion fluid 110, for instance an infusion fluid located within an infusion container 112 (e.g., a bag, a membrane, or the like).

In an example, the infusion fluid 110 is transferred to the catheter 102, and the infusion fluid 110 facilitates removal of a thrombus, for example by macerating the thrombus (e.g., parting, dividing, breaking up, compressing thrombus or the like).

In an example, the catheter system 100 includes a pressure chamber 114. The pressure chamber 114 facilitates isolation of an internal volume 115 of the pressure chamber 114 from a surrounding environment (e.g., atmosphere, operating room, medical facility, or the like). The infusion container 112 is located in the pressure chamber 114 (e.g., within the internal volume 115), and the infusion container 112 is compressed within the pressure chamber 114. In some examples, the internal volume 115 is a space between the walls of the infusion container 112 and the pressure chamber 114 (e.g., a housing of the pressure chamber 114).

The pump 108 pressurizes and moves a working fluid 116 from a working fluid container 118 into the internal volume 115 of the pressure chamber 114 from the working fluid container 118. The infusion container 112 optionally isolates the infusion fluid 110 from the working fluid 116 as well as the pump 108. The pump 108 pressurizes the working fluid 116 within the pressure chamber 114. For instance, the pump 108 pressurizes the working fluid 116 in the pressure chamber 114 above an ambient pressure of a surrounding environment (e.g., such as atmospheric pressure). In another example, the pump 108 pressurizes the pressure chamber relative to an initial pressure level (e.g., a vacuum, near vacuum, negative pressure generated with the vacuum container 122 or the like).

The pressurization of the working fluid 116 applies a force to the infusion container 112, for example to compress the infusion container 112 and correspondingly pressurize the infusion fluid 110 within the infusion container 112. In an example, pressurization of the working fluid 116 moves the infusion fluid 110 from the infusion container 112 to the catheter 102. The force applied to infusion container 112 by the working fluid 116 compresses the infusion container 112. For example, the force applied by the working fluid 116 to the infusion container 112 is transferred to the infusion fluid 110 because the infusion container 112 is deformable (e.g., pliable, compressible, squeezable, includes a movable member such as a piston or the like). Accordingly, pressurizing the working fluid 116 pressurizes the infusion fluid 110 within the infusion container 112. The infusion fluid 110 is thereby pressurized indirectly by the pump 108, for example by pressurizing the working fluid 116 in the pressure chamber 114. The fluid mechanical network of the catheter system 100 is thereby isolated from direct communication with the pump 108 to realize a 'pumpless' system free of cleaning or replacement of a pump after one or more uses. Instead, the pump 108 is isolated from the infusion fluid or other components of the system that are in direct or indirect contact with biological tissues or fluids.

Pressurizing the infusion fluid 110 within the infusion container 112 facilitates transfer of the infusion fluid 110 to the catheter 102. Accordingly, the pump 108 is not in communication with the infusion fluid 110. For example, the working fluid 116 flows through the pump 108, instead of the infusion fluid 110 flowing through the pump 108. Therefore, the infusion fluid is transferred to the catheter 102 according to the pressurization of the working fluid 116 within the pressure chamber 114 while the pump 108 remains isolated from the infusion fluid.

Indirectly pressurizing the infusion fluid 110 (e.g., by compressing the infusion container 112 in the pressure chamber 114) allows the pump 108 to be isolated from the infusion fluid 110. Isolating the pump 108 from the infusion fluid 110 facilitates reuse of the pump 108, for example because the infusion fluid 110 does not flow through or interact with the pump 108. The isolation of the infusion fluid 110 from the pump 108 allows the pump and working fluid to remain separated from the biologically exposed portions of the system 100 thereby allowing reuse of the pump 108, working fluid 116 or the like.

In an example, the infusion container 112 is interchangeable in the pressure chamber 114, thereby facilitating the reuse of the pump 108 (and other components of the catheter system 100). For instance, the infusion container 112 shown in FIG. 1 is a first infusion container including a first volume of the infusion fluid 110. The first infusion container 112 is removed from the pressure chamber 114. A second infusion container including a second volume of the infusion fluid 110 (or a different infusion fluid) is located in the pressure chamber 114. The pump 108 pumps the working fluid 116 into the pressure chamber 114 and thereby pressurizes the working fluid 116 and the isolated infusion fluid 110. Accordingly, the pump 108 is reusable because the working fluid 116 for the pump 108 is isolated from the infusion fluid 110 (e.g., by the infusion container 112). Thus, the working fluid 116 is not introduced into vasculature of the patient or exposed to the infusion fluid that does interact with the patient. The isolated working fluid 116 and the associated pump 108 thereby permit reuse of the pump 108 (and the working fluid 116). For instance, sterility of the infusion fluid 110 is maintained because the working fluid 116 flowing through the pump 108 indirectly pressurizes the infusion fluid 110 through the infusion container 112.

One or more lines 120 (e.g., tubing, or the like) facilitate operation of the catheter system 100 (or the drive unit 106). For example, the lines 120 establish fluidic communication between the drive unit 106 and the working fluid container 118. In another example, the lines 120 establish fluidic communication between the drive unit 106 and the pressure chamber 114. In yet another example, the lines 120 establish fluidic communication between the catheter 102 and the infusion container 112. For instance, the infusion fluid 110 is transferred from the infusion container 112 to the catheter 102 by the lines 120 (e.g., when the infusion container 112 is compressed by the working fluid 116).

In an example, the lines 120 provide isolated fluid channels that facilitate flow of fluid (or other material entrained therein) between components of the catheter system 100. For instance, the infusion fluid 110 in the lines 120 is isolated from fluid (or other material) in the lines 120 that flow to the vacuum collection container 122. Accordingly, the lines 120 facilitate flow of fluid through the system 100.

The catheter system 100 optionally includes a vacuum container 122. In an example, the vacuum container 122 facilitates removal of thrombus from the vasculature of a patient. For instance, the lines 120 establish fluidic communication between the vacuum source 104 and the vacuum container 122. The lines 120 further establish fluidic communication between the vacuum container 122 and the catheter 102. The vacuum source 104 provides a negative pressure (e.g., lower than blood pressure, lower than the pressure of the infusion fluid or the like), and facilitates drawing material into catheter 102. For example, the vacuum source 104 provides a vacuum to draw thrombus in the patient into the catheter 102. The thrombus material drawn into the catheter 102 by the vacuum flows through the lines 120 and into the vacuum container 122 to facilitate collection of the thrombus material (or other material and fluids drawn into the catheter by the vacuum source 104).

Accordingly, thrombus is removed from vasculature of a patient. In some examples, the vacuum container 122 includes the vacuum source 104. For instance, the vacuum container 122 is 'pre-charged' with a negative pressure lower than the pressure of one or more of the infusion fluid, blood pressure or the like (e.g., the vacuum container 122 is provided with a negative pressure relative to an ambient pressure), and the vacuum container 122 provides negative pressure to the lines 120 (and the associated catheter 102).

Components of the catheter system 100 are optionally coupled with an armature or housing (e.g., a stand, cart, dolly, or the like). For instance, one or more of the drive unit 106, the pressure chamber 114, the working fluid container 118, and the vacuum container 122 are coupled with the armature 124. The armature 124 supports the components of the catheter system 100.

In the example shown in FIG. 1, the catheter system 100 includes a controller 126. The controller 126 facilitates operation of the catheter system 100. For instance, the controller 126 operates one or more of the vacuum source 104, the pump 108 or one or more valves interposed between components of the system 100. In an example, the controller 126 operates the pump 108 (or the vacuum source 104) to provide a negative pressure in the pressure chamber 114 (e.g., by evacuating air from the pressure chamber 114). For example, the pump optionally withdraws the working fluid from the pressure chamber 114. In another example, the vacuum source 104 facilitates evacuation of air (or other fluids) from the pressure chamber 114, for example before pumping the working fluid into the internal volume 115. In some examples, the controller 126 operates the pump 108 to pressurize (e.g., raise pressure) the working fluid 116 and deliver the working fluid from the working fluid container 118 to the pressure chamber 114. The pump 108 pressurizes the working fluid 116 in the pressure chamber 114. In another example, the pump 108 is operated to remove the working fluid 116 from the pressure chamber 114 (e.g., by generating a negative pressure and pumping the working fluid 116 into the working fluid container 118). The system 100 includes controls that cooperate with the controller to operate the system 100. The system 100 optionally includes a display that provides information about the system 100.

As described herein, the lines 120 facilitate transfer of the infusion fluid 110 to the catheter 102. For example, the lines 120 establish fluidic communication between the catheter 102 and infusion container 112. The catheter system 100 optionally includes a spike 128 that is in communication with the lines 120 and engages with the infusion container 112. For example, the spike 128 pierces (e.g., punctures, inserts into, penetrates, or the like) the infusion container 112 and establishes fluidic communication between the infusion bag 112 and the lines 120.

The spike 128 is optionally rigid. For instance, the spike 128 is rigid in comparison to the infusion container 112 that is deformable. In an example, the spike 128 has a higher durometer in comparison the infusion container 112. In another example, the infusion container 112 includes a polyvinyl chloride bag and the spike 128 includes stainless steel. Optionally, a fitting such as a gasket, clamp or the like, is proximate to the spike 128 and provides a sealed interconnection between the spike 128 and the infusion container 112.

The rigidity of the spike 128 facilitates transfer of the infusion fluid 110 to the catheter 102. For example, the spike 128 resists compression when the working fluid 116 is pressurized in the pressure chamber 114. For instance, the infusion container 112 is compressed with the pressurized working fluid, thereby pressurizing the infusion container 112 and the infusion fluid 110 therein. The spike 128 resists compression to permit consistent flow of the infusion fluid 110 through the spike 128 (and into the lines 120 and the catheter 102). For instance, the spike 128 resists occlusion when the working fluid 116 is pressurized and the infusion container 112 is compressed.

In some examples, the catheter system 100 includes a seal 130. The seal 130 facilitates the fluidic communication between the catheter 102 and the infusion container 112. As described herein, the internal volume 115 of the pressure chamber 114 is isolated from the surrounding environment. The seal 130 allows the catheter 102 to communicate with the infusion container 112 while isolating the internal volume 115 of the pressure chamber 114 from the infusion fluid 110 and the environment external to the pressure chamber 114 (e.g., ambient air). In an example, the spike 128 extends into the internal volume 115 (or the infusion container 112) from an exterior of the pressure chamber 114. The seal 130 engages with the spike 128 to isolate the internal volume 115 from the surrounding environment (e.g., ambient air surrounding the system 100). For example, the spike 128 includes a flange, and the seal 130 includes one or more o-rings that engage with the spike 128 (e.g., the flange of the spike 128) to facilitate isolation of the internal volume 115. Accordingly, the seal 130 facilitates transfer of the infusion fluid 110 to the catheter 102 from the infusion container 112 while maintaining the isolation of the internal volume 115.

As described herein, the infusion container 112 is interchangeable in the pressure chamber 114. For instance, the pressure chamber 114 includes a hinge 132. The hinge 132 facilitates relative movement between components between components of the pressure chamber 114. In an example, the hinge 132 allows a relative movement between a first portion (e.g., a door, or the like) of the pressure chamber 114 and a second portion (e.g., a housing, frame, or the like) of the pressure chamber 114. For instance, the pressure chamber 114 includes a clamp 134, and the clamp 134 facilitates securing the first portion of the pressure chamber 114 to the second portion of the pressure chamber 114. Accordingly, the pressure chamber facilitates interchanging of the infusion container 112 while facilitating isolation of the internal volume 115 from the surround environment.

Figure 2:
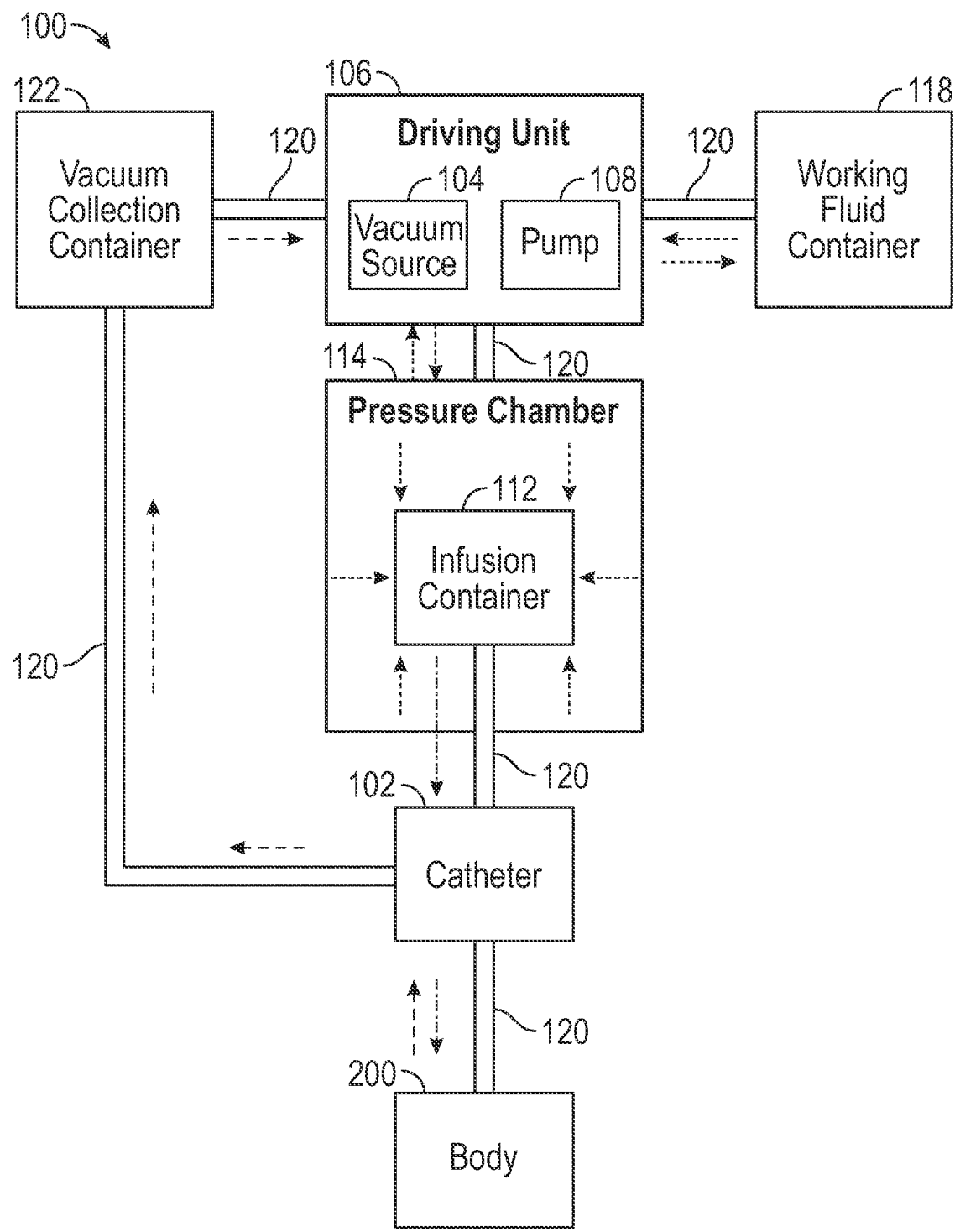
FIG. 2 illustrates a schematic diagram of the catheter system.

FIG. 2 illustrates a schematic diagram of the catheter system 100. As described herein, the catheter system 100 includes one or more of the catheter 102, the drive unit 106, the working fluid container 118, and the vacuum collection container 122. The catheter 102 is optionally inserted into vasculature of a body 200 of a patient. The catheter 102 provides access to the vasculature of the body 200. For instance, the catheter 102 facilitates infusion of the infusion fluid 110 (shown in FIG. 1) into the body 200.

The one or more lines 120 facilitate transfer of material (e.g., the infusion fluid 110, thrombus, blood, or the like) within the catheter system 100. In an example, the pump 108 pumps working fluid from the working fluid container 118 to the pressure chamber 114. The lines 120 provide unidirectional flow, or bi-directional flow between components of the catheter system 100. For example, the lines 120 include a check valve to facilitate unidirectional flow in the lines 120. In another example, the lines 120 include one or more lumens between the components. For instance, the pump 108 pumps the working fluid 116 (shown in FIG. 1) from the working fluid container 118 to the pressure chamber 114 through a first lumen of the lines 120. The pump pumps the working fluid 116 from the pressure chamber 114 to the working fluid container 118 through a second lumen of the lines 120 (e.g., for evacuation of the pressure chamber 114).

The catheter 102 facilitates removal of material (e.g., thrombus, blood, previous infused infusion fluid or the like) from the vasculature of the body 200. For instance, catheter 102 is in fluidic communication with the vacuum collection container 122, and the vacuum source 104 draws material (by way of relative negative pressure) from the body 200 into the catheter 102 and into the vacuum collection container 122.

Figure 3:
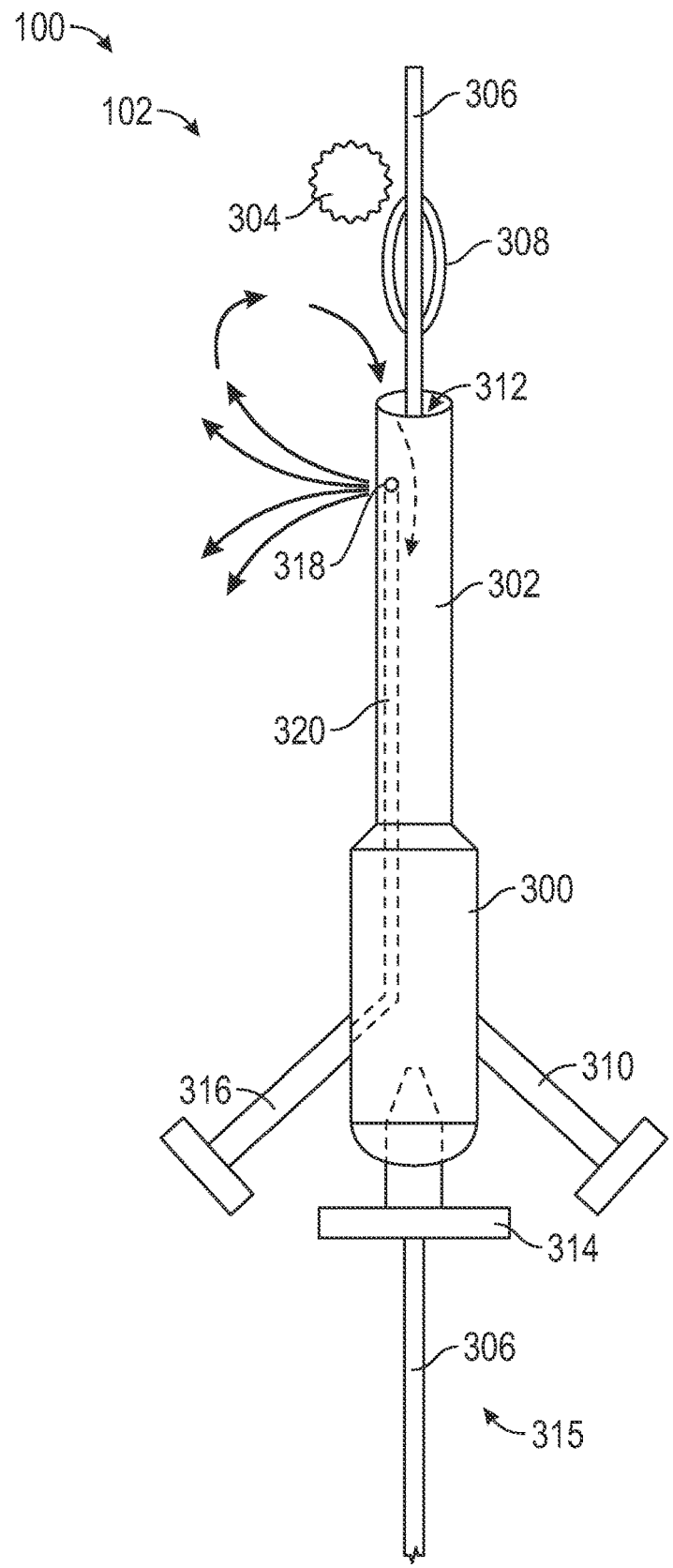
FIG. 3 illustrates a side view of the catheter system.

FIG. 3 illustrates a side view of the catheter system 100. In an example, the catheter 102 includes a supply manifold 300 (e.g., a hub) and a catheter body 302 coupled to the supply manifold 300. The catheter body 302 is inserted into vasculature of the body 200 (shown in FIG. 2). In an example, the catheter body 302 provides access to the vasculature, for instance to remove thrombus 304 in the body 200 of the patient including maceration (e.g., parting, dividing, breaking up, compressing thrombus or the like).

As shown in FIG. 3, the catheter system 100 includes a guidewire 306, and the guidewire 306 facilitates maceration of the thrombus 304, for instance with mechanical interaction. The guidewire 306 optionally includes a disruptor 308 (e.g., one or more strands, wires, a cage, or the like). The guidewire 306 (and the disruptor 308) mechanically engage with the thrombus 304, for example to macerate thrombus 304 into a plurality of pieces readily drawn into the catheter for extraction from the vasculature.

In some examples, the supply manifold 300 includes a vacuum supply port 310, and the vacuum supply port 310 is in fluidic communication with the vacuum source 104 (shown in FIG. 1). For example, the lines 120 facilitate fluidic communication of the vacuum source 104 with the vacuum supply port 310. The vacuum supply port 310 is in fluidic communication with a suction lumen 312 of the catheter body 302. Accordingly, the vacuum source 104 provides a vacuum within the suction lumen 312, for instance to remove thrombus 304 from the body 200 (shown in FIG. 2) of a patient. In some examples, the supply manifold 300 includes a seal 314 such as a pliable septum, lip seal, diaphragm or the like. The seal 314 engages with the guidewire 306 to minimize fluid passage between the guidewire 306 and the suction lumen 312 and thereby enhance the negative pressure applied suction lumen 312.

In another example, the supply manifold 300 includes an infusion port 316, and the infusion port 316 is in fluidic communication with the infusion container 112 (shown in FIG. 1). For example, the lines 120 facilitate transfer of the infusion fluid 110 (shown in FIG. 1) to the infusion port 316 of the catheter 102.

The catheter 102 optionally includes an infusion nozzle 318. The infusion nozzle 318 provides the infusion fluid 110, for example by discharging the infusion fluid 110 from the infusion nozzle 318. In an example, the infusion nozzle 318 is included in the catheter body 302, and the infusion fluid 110 is discharged at one or more locations along the catheter body 302. For instance, the catheter 102 optionally includes two or more infusion nozzles 318.

The infusion nozzle 318 is in fluidic communication with the infusion port 316 of the supply manifold 300. For instance, the catheter 102 includes an infusion lumen 320, and the infusion lumen 320 facilitates transfer of infusion fluid 110 from the infusion port 316 to the infusion nozzle 318. In an example, the infusion lumen 320 is isolated from the suction lumen 312. For instance, the flow of infusion fluid 110 is isolated from direct communication (e.g., suction, or the like) with the suction lumen 312. Removal of the thrombus 304 is enhanced, for instance because the infusion fluid 110 discharged by the infusion nozzle 318 engages initially with thrombus in the vasculature and is then drawn into the suction lumen 312 (e.g., as denoted by the arrows in FIG. 3) toward the suction lumen 312.

In an example, the infusion lumen 320 facilitates transfer of the infusion fluid 110 to the infusion nozzle 318, for example to facilitate discharge of the infusion fluid 110. Discharging infusion fluid 110 facilitates maceration of the thrombus 304, for example by engaging with the thrombus 304 to mechanically (including fluid mechanically) separate the thrombus 304 into a plurality of pieces. The infusion fluid 110 is optionally discharged at a relatively higher pressure (in comparison to ambient blood pressure) from the infusion nozzle 318 to facilitate maceration of the thrombus 304. Discharging infusion fluid 110 facilitates removal of thrombus 304, for instance by entraining the thrombus 304 with the infusion fluid 110 (e.g., a piece of the thrombus 304 intermixed with the infusion fluid 110 or the like). The entrained thrombus is drawn into the suction lumen 312 according to the relatively lower pressure therein.

In an example, the catheter system 100 pressurizes the infusion fluid to 1,000 pounds per square inch (however the present subject matter is not so limited). In some approaches, the infusion fluid is pressurized to 10,000 pounds per square inch. Isolating the infusion lumen 320 from the suction lumen 312 facilitates a reduction in pressure for the catheter system 100, for instance because the vacuum source 104 generates a vacuum that is isolated from the flow of infusion fluid in the infusion lumen 320.

Figure 4:
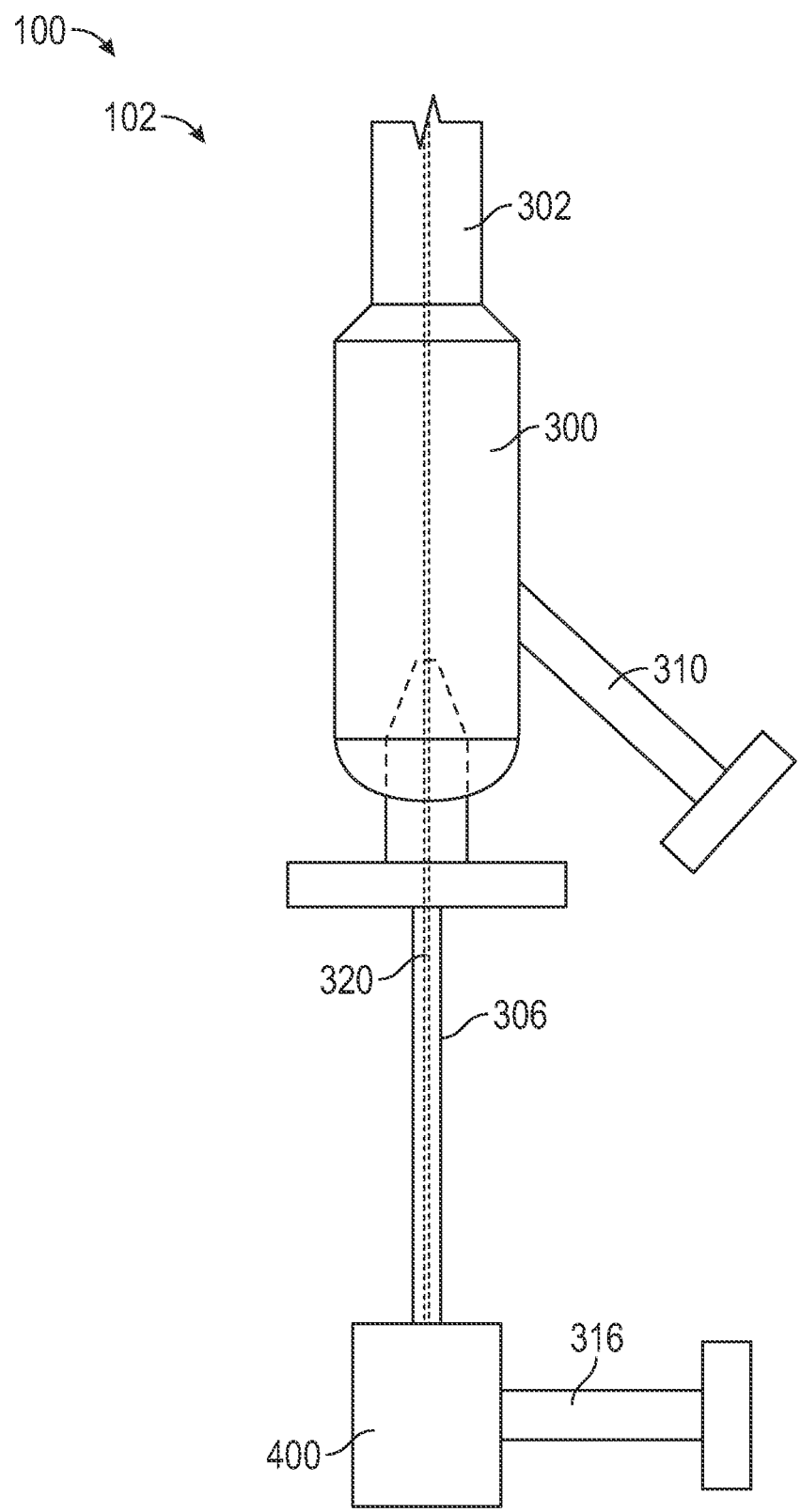
FIG. 4 illustrates a side view of another example of the catheter system including a catheter.

FIG. 4 illustrates a side view of another example of the catheter system 100 including the catheter 102. In some examples, the infusion lumen 320 is included in the guidewire 306. For instance, the guidewire 306 is coupled with an infusion hub 400, and the infusion hub 400 includes the infusion port 316. The infusion port 316 is in fluidic communication with the infusion lumen 320. In an example, the infusion fluid 110 (shown in FIG. 1) flows into the infusion lumen 320 from the infusion port 316. Accordingly, the infusion lumen 320 facilitates flow of the infusion fluid 110 within the guidewire 306.

The guidewire 306 is optionally received in the catheter body 302 (and the supply manifold 300). For example, the guidewire 306 is located in the suction lumen 312 (shown in FIG. 3). The infusion lumen 320 is isolated from the suction lumen 312, for example because the infusion lumen 320 is located in the guidewire 306. Accordingly, a negative pressure generated in the suction lumen 312 (e.g., provided by the vacuum source 104 in communication with the vacuum supply port 310) is isolated from infusion fluid 110 flowing in the infusion lumen 320.

Figure 5:
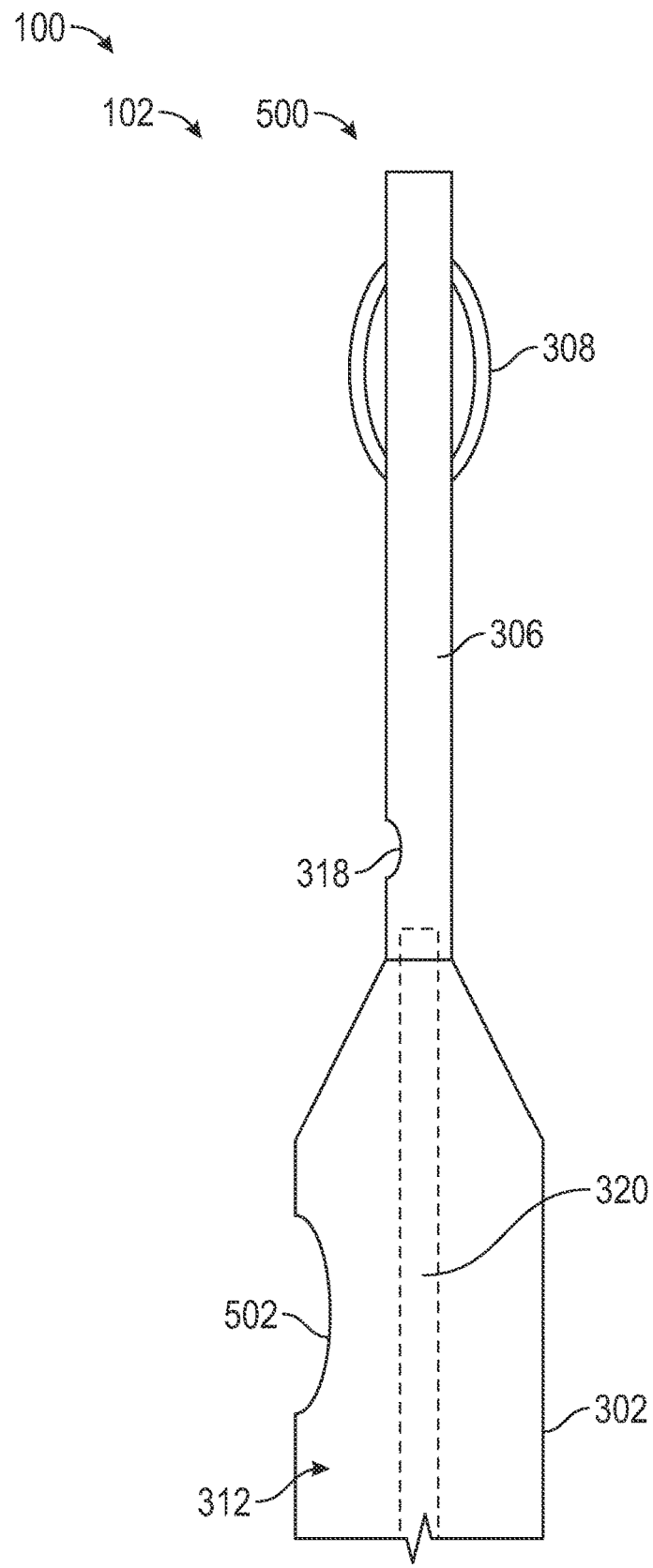
FIG. 5 illustrates a side view of a distal end of the catheter of FIG. 4.

FIG. 5 illustrates a side view of a distal end 500 of the catheter 102 of FIG. 4. The distal end 500 of the catheter 102 is opposite to the proximal end 315 (shown in FIG. 3) of the catheter 102. As described herein, the infusion lumen 320 is in communication with the infusion nozzle 318. For instance, the guidewire 306 includes one or more of the infusion nozzle 318, and the infusion fluid 110 (shown in FIG. 1) is discharged from the guidewire 306 at the infusion nozzle 318.

In an example, the catheter system 100 includes one or more suction ports 502. For instance, the suction port 502 extends through the catheter body 302, and the suction port 502 is in fluidic communication with the suction lumen 312. In another example, the suction port 502 includes an open end of the catheter body 302. In some examples, a negative pressure in the suction lumen 312 draws material through the suction port 502 and into the suction lumen 312 (e.g., to facilitate removal of the material from vasculature of a patient).

The infusion fluid 110 discharged at the infusion nozzle 318 optionally flows to the suction port 502. For example, the infusion fluid 110 discharged at the infusion nozzle 318 entrains one or more pieces thrombus (e.g., macerated thrombus, or the like) from the vasculature. For instance, the disruptor 308 engages with a thrombus to macerate the thrombus including, but not limited to, dislodging, parting, dividing, freeing, compressing, breaking up, or the like. The infusion fluid 110 discharged at the infusion nozzle 318 further removes the thrombus, for instance through fluid mechanical maceration, and entrains the thrombus for passage to the suction lumen 312. In one example, the macerated thrombus is captured or entrained in fluid flow between the infusion nozzle 318 and the suction port 502.

Figure 6:
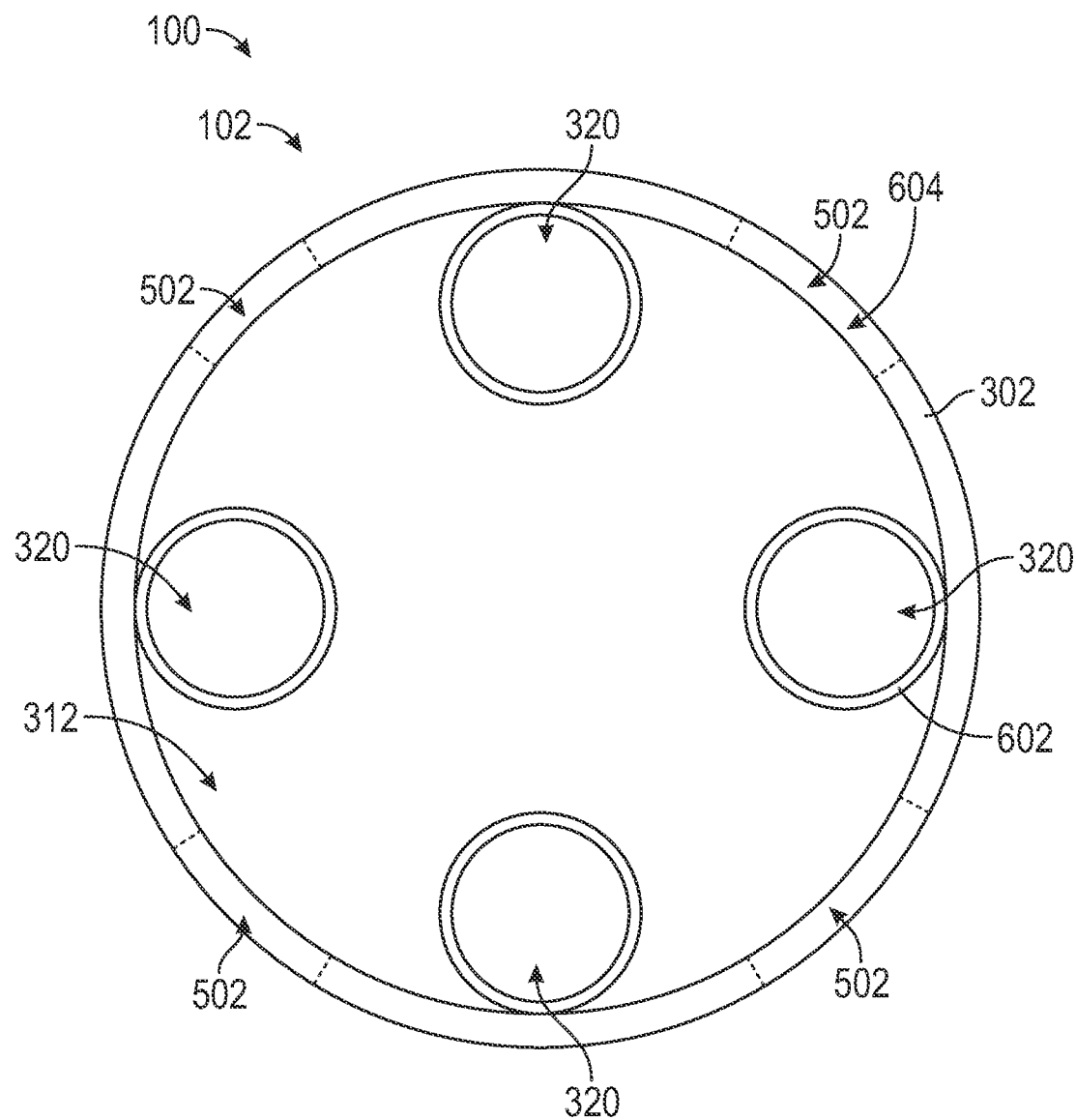
FIG. 6 illustrates a cross-sectional view of the catheter.

FIG. 6 illustrates a cross-sectional view of the catheter 102. As described herein, the catheter 102 optionally includes one or more of the infusion nozzle 318 (shown in FIG. 3). For instance, the catheter 102 includes a plurality of infusion lumens 320 (e.g., the catheter 102 includes two or more of the infusion lumen 320). The infusion lumens 320 are isolated from the suction lumen 312, for example with an infusion lumen wall 602. Optionally, the infusion lumens 320 are included within the sidewall of the catheter body 302, for instance the catheter body 302 is extruded with the lumens 600, and the body 302 is a multi-layer assembly including lumen liners therein or the like.

In some examples, the catheter 102 includes a plurality of suction ports 604 (e.g., the catheter 102 includes two or more of the suction port 502). The suction ports 604 extend through the sidewall of the catheter body 302. As described herein, the suction ports 604 are in communication with the suction lumen 312, and the suction ports 604 facilitate removal of material, for instance removal of thrombus from vasculature of a patient.

Figure 7C:
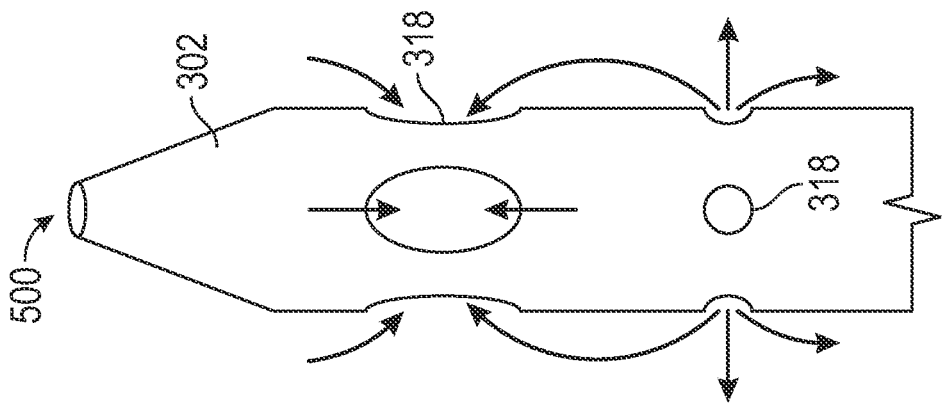
FIG. 7C illustrates a side view of still yet another example of the catheter.
Figure 7B:
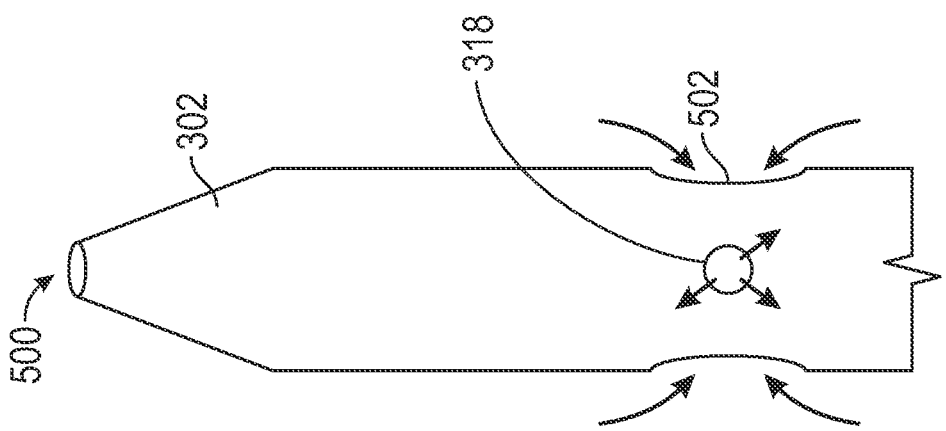
FIG. 7B illustrates a side view of yet another example of the catheter.
Figure 7A:
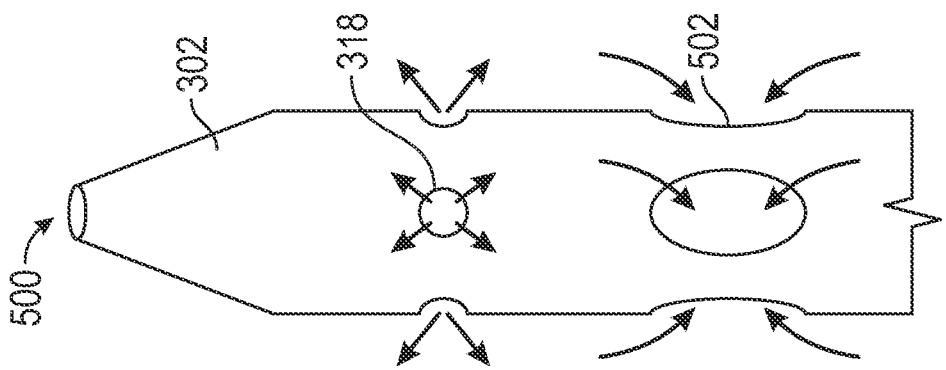
FIG. 7A illustrates a side view of another example of the catheter.

FIGS. 7A-7C illustrate side views of examples of the catheter 102. As discussed herein, the catheter 102 (including the catheter body 302) includes a distal end 500. The arrows proximate the infusion nozzle 318 and the suction port 502 in FIGS. 7A-7C indicate flow of infusion fluid 110 (shown in FIG. 3) proximate to the catheter 102.

In some examples, the infusion nozzle 318 is located distal to the suction port 502 (shown in FIG. 7A). Accordingly, infusion fluid 110 is discharged from the infusion nozzle 318, and the negative pressure in the suction lumen 312 draws the infusion fluid (or other material, for instance blood, thrombus, or the like) toward the proximal end 315 (shown in FIG. 3) and into the suction port 502. In another example, the infusion port 316 is located proximal to the suction port 502 (shown in FIG. 7C. The infusion fluid 110 (shown in FIG. 1) is discharged by the infusion nozzle 318, and the negative pressure in the suction lumen 312 draws the infusion fluid toward the distal end 500 and into the suction port 502. The infusion nozzle 318 is optionally aligned with the suction port 502 (shown in FIG. 7B). Accordingly, infusion fluid 110 optionally flows radially (and proximally) from the infusion nozzle 318 to the suction port 502. The infusion nozzle 318 and the suction port 508 work cooperatively to enhance capture of thrombus (or other material) with the catheter system 100, for instance because the infusion nozzle 318 and the suction port 502. The flow of infusion fluid between the one or more infusion ports 318 and the one or more suction ports 502 entrains thrombus, optionally macerates thrombus, and guides entrained thrombus into the suction ports 502 and associated suction lumen.

Figure 8C:
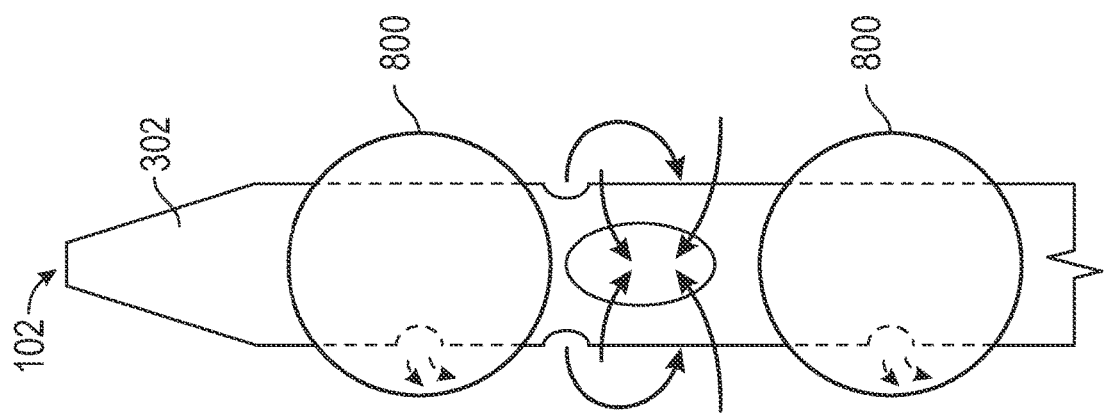
FIG. 8C illustrates a side view of a still further example of the catheter.
Figure 8B:
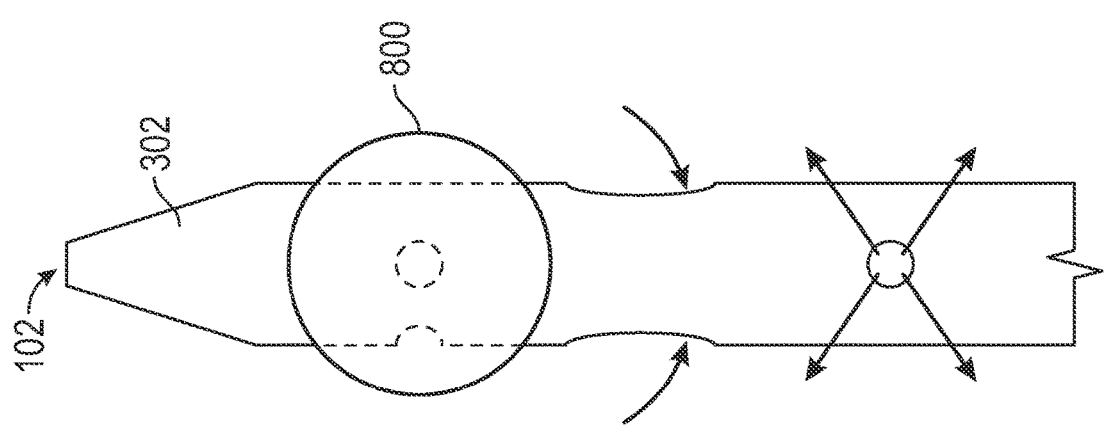
FIG. 8B illustrates a side view of an additional example of the catheter.
Figure 8A:
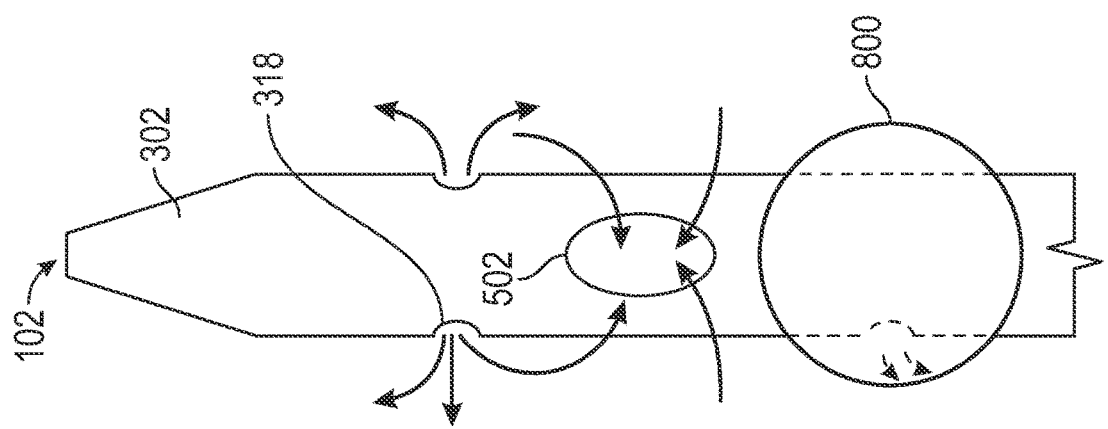
FIG. 8A illustrates a side view of a further example of the catheter.

FIGS. 8A-8C illustrate side view of examples of the catheter 102. In an example, the catheter 102 includes one or more expandable balloons 800. For instance, the expandable balloons 800 are coupled with the catheter body 302. The balloons 800 facilitate capture of material, for example thrombus in vasculature of a patient. The balloons 800 are optionally expanded while located in the vasculature of the patient, and in the expanded configuration, the balloons 800 facilitate capture of thrombus (or macerated thrombus) with the catheter system 100. For example, the balloons 800 engage with walls of the vasculature of the patient, and the engagement by the balloons 800 inhibits the macerated thrombus from escaping (thereby facilitating drawing the macerated thrombus into the suction lumen 312).

The balloons 800 are optionally in communication with the infusion nozzle 318. Accordingly, flow (or pressurizing) of the infusion fluid 110 (shown in FIG. 1) optionally causes the balloons 800 to expand. In an example, a reduction in flow (or pressure) of the infusion fluid 110 causes the balloons 800 to contract.

In an example, the balloons 800 are located distally of the suction port 502 or the infusion nozzle 318 (shown in FIG. 8B). In another example, the balloons 800 are located proximal of the suction port 502 or the infusion nozzle 318 (shown in FIG. 8A). In yet another example, the balloons 800 are located distal to and proximal to the suction port 502 or the infusion nozzle 318 (shown in FIG. 8C). For example, the balloons 800 straddle the suction port 502 and the infusion nozzle 318.

As described herein, the balloons 800 enhance capture of thrombus with the catheter system 100. For example, the balloons are located proximate to the thrombus. The balloons 800 optionally straddle the thrombus. Accordingly, the balloons 800 facilitate containing the thrombus, and inhibit escape of the thrombus (or macerated thrombus). Accordingly, removal of the thrombus is enhanced, for instance because the thrombus is contained by the balloons 800. The containment provided by the balloons 800 facilitates drawing the thrombus into the suction lumen 312 (shown in FIG. 6) and into the vacuum collection container 122 (shown in FIG. 1). For example, the thrombus is not allowed to escape due to the containment provided by the balloons, which facilitates drawing the thrombus into the suction lumen 312.

Figure 9:
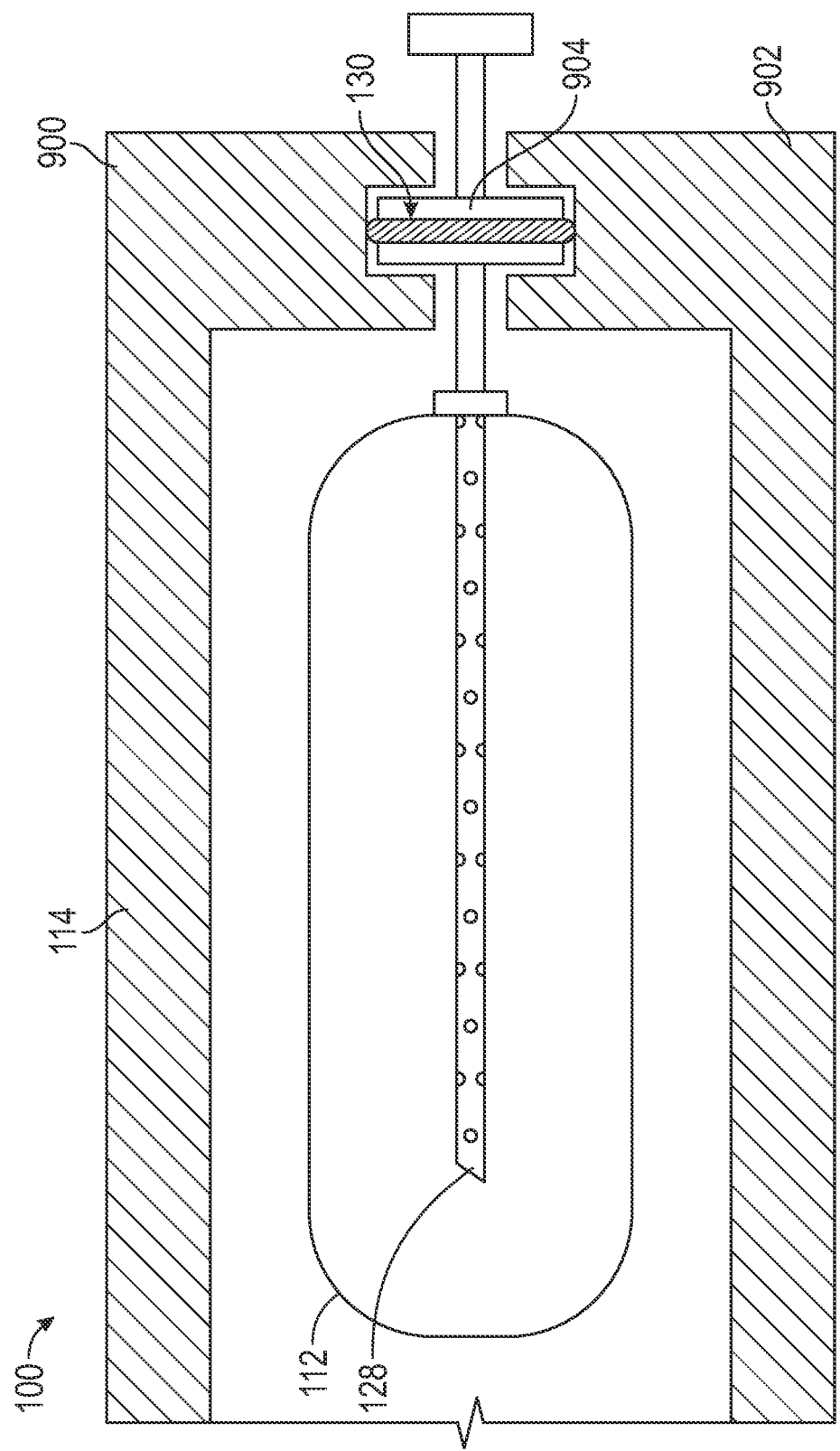
FIG. 9 is a cross-sectional view of a pressure chamber.

FIG. 9 is a cross-sectional view of the pressure chamber 114. In an example, the infusion container 112 is located in or received in the pressure chamber 114. The spike 128 punctures the infusion container 112, and the spike facilitates the transfer of the infusion fluid in the infusion container to the catheter 102 located outside the pressure chamber 114.

The seal 130 facilitates isolating the internal volume from the surrounding environment (e.g., to inhibit leakage proximate the spike 128). In an example, a first section 900 of the pressure chamber 114 is moveable relative to a second section 902 of the pressure chamber 114. The seal 130 is optionally coupled with a flange 904 of the spike 138, and the seal 130 is compressible between the sections 900, 902 of the pressure chamber 114 and the flange 904. Accordingly, the seal 130 cooperates with the spike 128 and the pressure chamber 114 to isolate the internal volume 115 while facilitating transfer of infusion fluid from the infusion container 112.

VARIOUS NOTES & ASPECTS

Example 1 is a thrombectomy catheter system, comprising: a catheter configured for insertion into vasculature of a patient; a pressure chamber configured to isolate an internal volume from a surround environment; an infusion container including an infusion fluid, wherein the infusion container is configured for reception in the pressure chamber; a drive unit configured to pressurize a working fluid in the pressure chamber with the infusion container received in the pressure chamber, wherein the pressurizing of the working fluid correspondingly compresses the infusion container to pressurize the infusion fluid and transfer the infusion fluid to the catheter; and wherein the infusion fluid is isolated from the working fluid by the infusion container when the working fluid is pressurized in the pressure chamber.

In Example 2, the subject matter of Example 1 optionally includes a working fluid contained configured to supply the working fluid.

In Example 3, the subject matter of any one or more of Examples 1-2 optionally include a spike configured to pierce the infusion container, wherein the infusion spike facilitates fluidic communication between the infusion container and the catheter.

Example 4 is a thrombectomy catheter configured to remove thrombus from vasculature of a patient, the thrombectomy catheter comprising: a catheter body configured for insertion into the vasculature of the patient; a suction lumen configured to provide a vacuum at a suction port; an infusion lumen configured to provide an infusion fluid, wherein the suction lumen is isolated from the infusion lumen; an infusion port configured to discharge the infusion fluid from the infusion body; and wherein the catheter is configured to draw the infusion fluid discharged from the infusion body into the suction port.

In Example 5, the subject matter of Example 4 optionally includes an expandable balloon configured to engage with the vasculature and contain the thrombus and enhance drawing the thrombus into the suction port.

Each of these non-limiting examples can stand on its own, or can be combined in various permutations or combinations with one or more of the other examples.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A thrombectomy catheter system comprising:
   a catheter configured to be inserted into vasculature of a patient;
   a pressure chamber configured to isolate an internal volume from a surrounding environment;
   an infusion container including an infusion fluid and configured to be received within the pressure chamber;
   a vacuum collection container configured to be in fluid communication with a suction lumen of the catheter; and
   a drive unit configured to pressurize a working fluid in the pressure chamber with the infusion container received in the pressure chamber, wherein the pressurizing of the working fluid correspondingly compresses the infusion container to pressurize the infusion fluid and transfer the infusion fluid to the catheter;
   wherein the drive unit includes a vacuum source configured to be in pressure-reducing communication with the vacuum collection container; and
   wherein the infusion fluid is isolated from the working fluid by the infusion container when the working fluid is pressurized in the pressure chamber.

2. The thrombectomy catheter system of claim 1, further comprising a fluid container configured to supply the working fluid.

3. The thrombectomy catheter system of claim 1, further comprising a spike configured to pierce the infusion container, wherein the piercing facilitates fluidic communication between the infusion container and the catheter.

4. The thrombectomy catheter system of claim 3, wherein
   (a) the spike is configured to puncture the infusion container, and
   (b) the spike has greater rigidity than the infusion container, thereby preventing occlusion of the infusion fluid through the spike during the pressurization of the working fluid.

5. The thrombectomy catheter system of claim 4, wherein
   (a) the infusion container is comprised of a polyvinyl chloride bag, and
   (b) the spike is comprised of stainless steel.

6. The thrombectomy catheter system of claim 4, further including a seal in sealing engagement between the spike and the pressure chamber, thereby facilitating isolation of the internal volume from the surrounding environment.

7. The thrombectomy catheter system of claim 1, wherein the infusion container is configured to be deformed by way of the compression.

8. The thrombectomy catheter system of claim 1, wherein
   (a) the drive unit includes a pump to cause the pressurization of the working fluid, and
   (b) the infusion container isolates the infusion fluid from the pump.

9. The thrombectomy catheter system of claim 8, wherein the pump is a positive displacement pump, a peristaltic pump or a syringe.

10. The thrombectomy catheter system of claim 1, wherein the infusion container is configured to be removed from the pressure chamber and replaced thereat by a second infusion container.

11. The thrombectomy catheter system of claim 1, wherein the vacuum collection container is pre-charged with a lower internal pressure than the surrounding environment.

12. The thrombectomy catheter system of claim 1, further comprising an armature to which one or more of the drive unit, pressure chamber, working fluid container, or the vacuum container are coupled.

13. The thrombectomy catheter system of claim 1, further comprising a controller configured to operate one or more of the vacuum source, a pump, or one or more valves within the system.

14. The thrombectomy catheter system of claim 13, wherein the vacuum source or the pump is further configured to facilitate evacuation of pressure or working fluid from the pressure chamber.

15. The thrombectomy catheter system of claim 1, wherein the pressure chamber includes (a) a hinge configured to facilitate relative movement between a first portion of the pressure chamber and a second portion of the pressure chamber, thereby allowing the infusion container to be moved between the internal volume and the surrounding environment for replacement of the infusion container, and (b) a clamp configured to selectedly secure the first portion from the relative movement with the second portion, thereby facilitating isolation of the internal volume from the surrounding environment.

16. The thrombectomy catheter system of claim 1, wherein the system is configured to pressurize the infusion fluid to between 1000 PSI and 10,000 PSI by way of the pressurization of the working fluid.

* * * * *